(12) United States Patent
Lan et al.

(10) Patent No.: US 10,824,017 B2
(45) Date of Patent: Nov. 3, 2020

(54) THERMAL CROSSLINK MATERIAL, MANUFACTURE METHOD OF LIQUID CRYSTAL DISPLAY PANEL AND LIQUID CRYSTAL DISPLAY PANEL

(71) Applicant: Shenzhen China Star Optoelectronics Technology Co., Ltd., Shenzhen (CN)

(72) Inventors: Song Lan, Shenzhen (CN); Yungjui Lee, Shenzhen (CN)

(73) Assignee: SHENZHEN CHINA STAR OPTOELECTRONICS TECHNOLOGY CO., LTD., Shenzhen, Guangdong (CN)

(*) Notice: Subject to any disclaimer, the term of this patent is extended or adjusted under 35 U.S.C. 154(b) by 91 days.

(21) Appl. No.: 16/297,710

(22) Filed: Mar. 11, 2019

(65) Prior Publication Data

US 2019/0204635 A1    Jul. 4, 2019

Related U.S. Application Data

(62) Division of application No. 15/026,255, filed on Mar. 31, 2016, now Pat. No. 10,303,001.

(30) Foreign Application Priority Data

Jan. 29, 2016  (CN) .......................... 2016 1 0070586

(51) Int. Cl.
  *G02F 1/1337* (2006.01)
  *C07C 69/54* (2006.01)
  (Continued)

(52) U.S. Cl.
  CPC ............ *G02F 1/1337* (2013.01); *C07C 69/54* (2013.01); *C09K 19/30* (2013.01); *C09K 19/56* (2013.01);
  (Continued)

(58) Field of Classification Search
  CPC ............... G02F 1/1337; G02F 1/13439; G02F 1/136213; G02F 1/133703;
  (Continued)

(56) References Cited

FOREIGN PATENT DOCUMENTS

CN        105061213 A    * 11/2015

* cited by examiner

*Primary Examiner* — Ruiyun Zhang
(74) *Attorney, Agent, or Firm* — Leong C. Lei

(57) ABSTRACT

Disclosed are a thermal crosslink material, a manufacture method of a liquid crystal display panel, and a liquid crystal display panel. A structural formula of the thermal crosslink material is

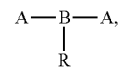

wherein A is

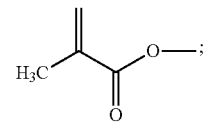

B is

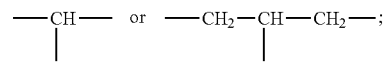

and R is a linear or chain branched alkyl having 5-20 C atoms, wherein one or more $CH_2$ in the alkyl is substituted with phenyl, cycloalkyl, —O—, —CONH—, —COO—, —O—CO—, —CO—, or —CH=CH— group, or one or more H atoms in the first group are substituted with F atom or Cl atom; a specific crosslink material may be one of (Continued)

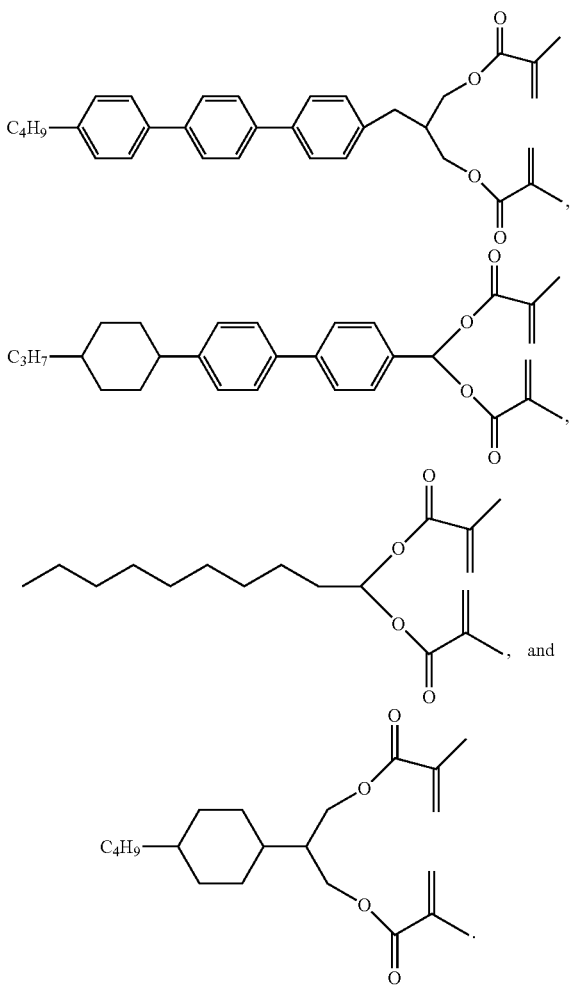

Molecules of the thermal crosslink material crosslink together to form a polymer having a crosslinked network, and groups A and B can be anchored on a substrate surface. The branch R provides an effect of vertical alignment and can form alignment films.

1 Claim, 5 Drawing Sheets

(51) Int. Cl.
  *C09K 19/56* (2006.01)
  *C09K 19/30* (2006.01)
  *G02F 1/1343* (2006.01)
  *G02F 1/1362* (2006.01)
  *C09K 19/04* (2006.01)
  *C09K 19/54* (2006.01)

(52) U.S. Cl.
  CPC .... *G02F 1/13439* (2013.01); *G02F 1/136213* (2013.01); *C07C 2601/14* (2017.05); *C09K 2019/0448* (2013.01); *C09K 2019/546* (2013.01); *C09K 2323/00* (2020.08); *C09K 2323/02* (2020.08); *G02F 1/133703* (2013.01); *G02F 1/133707* (2013.01); *G02F 2202/022* (2013.01)

(58) Field of Classification Search
  CPC ......... G02F 1/133707; G02F 2202/022; C07C 69/54; C07C 2601/14; C09K 19/30; C09K 19/56; C09K 2019/0448; C09K 2019/546; Y10T 428/10; Y10T 428/1005
  USPC ......... 428/1.1, 1.2, 1.23; 349/123, 131, 190, 349/191
  See application file for complete search history.

THERMAL CROSSLINK MATERIAL, MANUFACTURE METHOD OF LIQUID CRYSTAL DISPLAY PANEL AND LIQUID CRYSTAL DISPLAY PANEL

CROSS REFERENCE TO RELATED APPLICATIONS

This is a divisional application of co-pending U.S. patent application Ser. No. 15/026,255, filed on Mar. 31, 2016, which is a national stage of PCT Application No. PCT/CN2016/074615, filed on Feb. 26, 2016, claiming foreign priority of Chinese Patent Application No. 201610070586.8, filed on Jan. 29, 2016.

FIELD OF THE INVENTION

The present invention relates to a display manufacture field, and more particularly to thermal crosslink material, a manufacture method of a liquid crystal display panel and a liquid crystal display panel.

BACKGROUND OF THE INVENTION

The TFT-LCD (Thin Film Transistor Liquid Crystal Display) possesses advantages of thin body, power saving and no radiation to be widely used in many application scopes. Most of the TFT-LCDs on the present market are back light type liquid crystal displays, which comprise a liquid crystal display panel and a back light module. The working principle of the liquid crystal display panel is to locate liquid crystal molecules between two parallel glass substrates. The light of back light module is reflected to generate images by applying driving voltages to control whether the liquid crystal molecules to be changed directions.

Generally, the liquid crystal display panel comprises a CF (Color Filter) substrate, a TFT (Thin Film Transistor) substrate, LC (Liquid Crystal) sandwiched between the CF substrate and TFT substrate and sealant. The formation process generally comprises: a forepart Array process (thin film, photo, etching and stripping), a middle Cell process (Lamination of the TFT substrate and the CF substrate) and a post module assembly process (Attachment of the driving IC and the printed circuit board). The forepart Array process is mainly to form the TFT substrate for controlling the movement of the liquid crystal molecules; the middle Cell process is mainly to add liquid crystal between the TFT substrate and the CF substrate; the post module assembly process is mainly the driving IC attachment and the integration of the printed circuit board. Thus, the liquid crystal molecules are driven to rotate and display pictures.

In the liquid crystal display panel, a layer of alignment film is formed on the thin film transistor substrate and a color film substrate in generally. After the alignment film contacts with the LC, it can make the LC have a pre-tilted angle in certain direction, and thus provide a loading angle (the pre-tilted angle has significant influence to the driving voltage, contrast, response time and view angle of the TFT-LCD) for the liquid crystal molecules. Polyimide (PI) is commonly chosen to be the material of the alignment film, which mainly has rubbing alignment type IP material and lighting alignment type IP material. However, either of the alignment materials has its own drawback. The rubbing alignment type IP material is to form the alignment film with Rubbing method. The Rubbing method is to use fabric roller to perform contacting directional mechanical friction on the macromolecular PI film surface. The energy provided by rubbing the macromolecular surface make the macromolecular main chain be aligned in direction due to the extension, and thus the interaction of the branch and the LC is controlled to align the LC in the direction of the pre-tilted angle; as rubbing, the issues of powder particles, residual electrostatic and brush marks reduce the process yield. The lighting alignment type IP material is to form the alignment film with photo-alignment technology. The photo-alignment technology is to utilize the photochemical reaction of the ultraviolet light polymer monomers to create the anisotropy, and the liquid crystal molecules and the alignment film surface branch interact with each other. For reaching the stable status of the minimum energy, the liquid crystal molecules are aligned along the direction of which the acted force is the maximum defined by the lighting alignment. The lighting alignment type IP material can solve the aforesaid problems but with the restriction of the material properties, the heat resistance and the aging resistance are poor, and meanwhile, the LC anchoring ability is weaker, the quality of the panel is influenced. Besides, the PI material itself has high polarity and high water absorption. The storage and the delivery can easily change the property to result in the nonuniform alignment. The price of the PI material is expensive, and the film formation process on the TFT-LCD is more complicated, which leads to the increase of the panel cost.

SUMMARY OF THE INVENTION

An objective of the present invention is to provide thermal crosslink material, employed to form the alignment films to reduce the production cost of the alignment films and promote the capacity.

Another objective of the present invention is to provide a manufacture method of a liquid crystal display panel, in which by adding the thermal crosslink material in the liquid crystal compound of the liquid crystal display panel to form the alignment films on the surfaces of opposite sides of the TFT substrate and the CF substrate to simplify the manufacture process and to reduce the production cost.

Another objective of the present invention is to provide a liquid crystal display panel, in which the alignment films are polymer, which is formed by that the thermal crosslink material mixed in the liquid crystal material is generated with the crosslinking reaction in a heating condition, and is deposed on the surfaces of opposite sides of the TFT substrate and the color film substrate, and the manufacture process is simple, and the production cost is low.

For realizing the aforesaid objectives, the present invention provides thermal crosslink material, employed to be alignment film material, and a structural formula thereof is

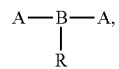

wherein
A is

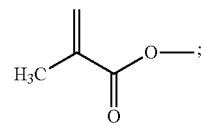

B is

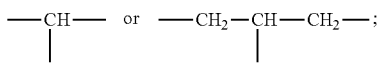

R is a linear or chain branched alkyl having 5-20 C atoms, and a first group obtained after some $CH_2$ group in the alkyl is replaced by phenyl, cycloalkyl, —O—, —CONH—, —COO—, —O—CO—, —CO—, or —CH=CH— group, or a second group obtained after the alkyl and some H atom in the first group are replaced by F atom or Cl atom.

A structural formula of thermal crosslink material is:

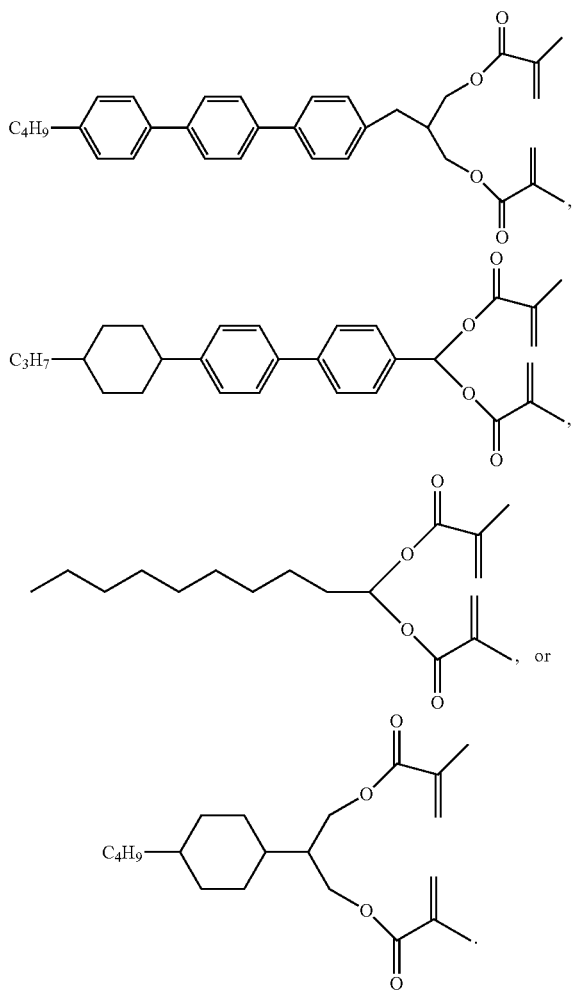

The present invention further provides a manufacture method of a liquid crystal display panel, comprising steps of:

step 1, mixing thermal crosslink material into liquid crystal material to obtain liquid crystal compound;

a structural formula of the thermal crosslink material is

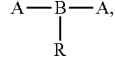

wherein
A is

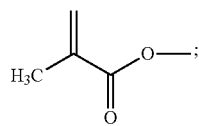

B is

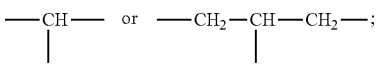

R is a linear or chain branched alkyl having 5-20 C atoms, and a first group obtained after some $CH_2$ group in the alkyl is replaced by phenyl, cycloalkyl, —O—, —CONH—, —COO—, —O—CO—, —CO—, or —CH=CH— group, or a second group obtained after the alkyl and some H atom in the first group are replaced by F atom or Cl atom;

step 2, providing a TFT substrate, and employing one drop filling to drop the liquid crystal compound obtained in the step 1 on one side of the TFT substrate;

step 3, providing a CF substrate, and employing one drop filling to drop seal on one side of the CF substrate to form a sealant;

step 4, oppositely vacuum laminating the TFT substrate and the CF substrate, and then the sealant and the liquid crystal compound are positioned between the TFT substrate and the CF substrate to obtain a cell;

step 5, irradiating the cell obtained in the step 4 with ultraviolet light, and then heating the same to cure the sealant, and in the heating process, the thermal crosslink material in the liquid crystal compound generates crosslinking reaction to form polymer, and with increase of polymer molecular weight, the polymer generates phase separation with the liquid crystal material to be deposed on the surfaces of opposite sides of the TFT substrate and the CF substrate to form the alignment films, wherein the branch part R in the polymer which is compatible with the liquid crystal acts a result of vertical alignment.

A structural formula of the thermal crosslink material is:

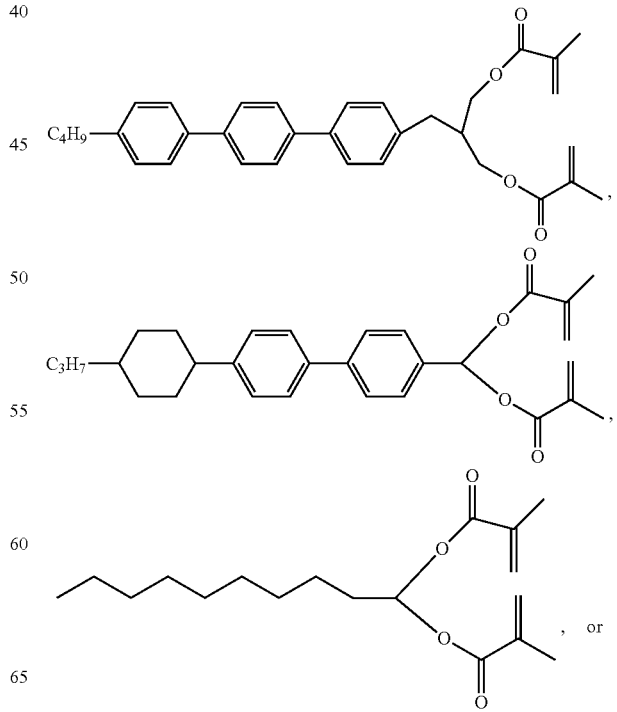

-continued

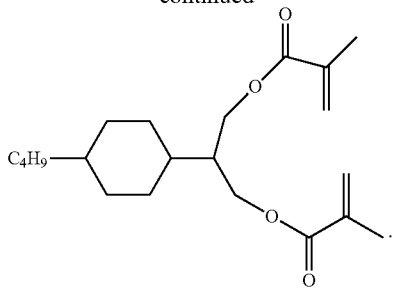

In the liquid crystal compound obtained in the step 1, a content of the thermal crosslink material is 0.1-5 wt %.

In the step 5, an irradiation intensity of the ultraviolet light is 50-100 mW/cm$^2$, and an irradiation period is 1-5 min, and a heating temperature is 110-130° C., and a heating period is 20-30 min.

The liquid crystal display panel is a multi-domain vertical alignment type liquid crystal display panel, and a plurality of roof shape projections are provided on the one side of the TFT substrate provided in the step 2 where the liquid crystal compound is pre-dropped, and a plurality of roof shape projections are provided on the one side of the CF substrate provided in the step 3 where the sealant is pre-dropped.

Pixel electrodes are provided on the one side of the TFT substrate provided in the step 2 where the liquid crystal compound is pre-dropped, and a common electrode is provided on the one side of the CF substrate provided in the step 3 where the sealant is pre-dropped.

The present invention further provides a liquid crystal display panel, comprising a TFT substrate and a CF substrate which are oppositely positioned, and a liquid crystal layer sandwiched between the TFT substrate and the CF substrate, a sealant employed for sealing the TFT substrate and the CF substrate, and alignment films formed at surfaces of the TFT substrate and the CF substrate facing the liquid crystal layer;

a plurality of roof shape projections are provided on sides of the TFT substrate and the CF substrate facing the liquid crystal layer;

the liquid crystal layer comprises liquid crystal material;

the alignment films are polymer, which is formed by that the thermal crosslink material mixed in the liquid crystal material is generated with the crosslinking reaction in a heating condition, and is deposed on the surfaces of opposite sides of the TFT substrate and the CF substrate;

a structural formula of the thermal crosslink material is

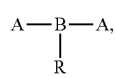

wherein
A is

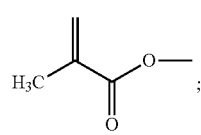

B is

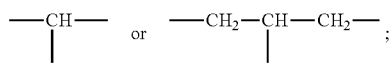

R is a linear or chain branched alkyl having 5-20 C atoms, and a first group obtained after some CH$_2$ group in the alkyl is replaced by phenyl, cycloalkyl, —O—, —CONH—, —COO—, —O—CO—, —CO—, or —CH=CH— group, or a second group obtained after the alkyl and some H atom in the first group are replaced by F atom or Cl atom.

A structural formula of the thermal crosslink material is:

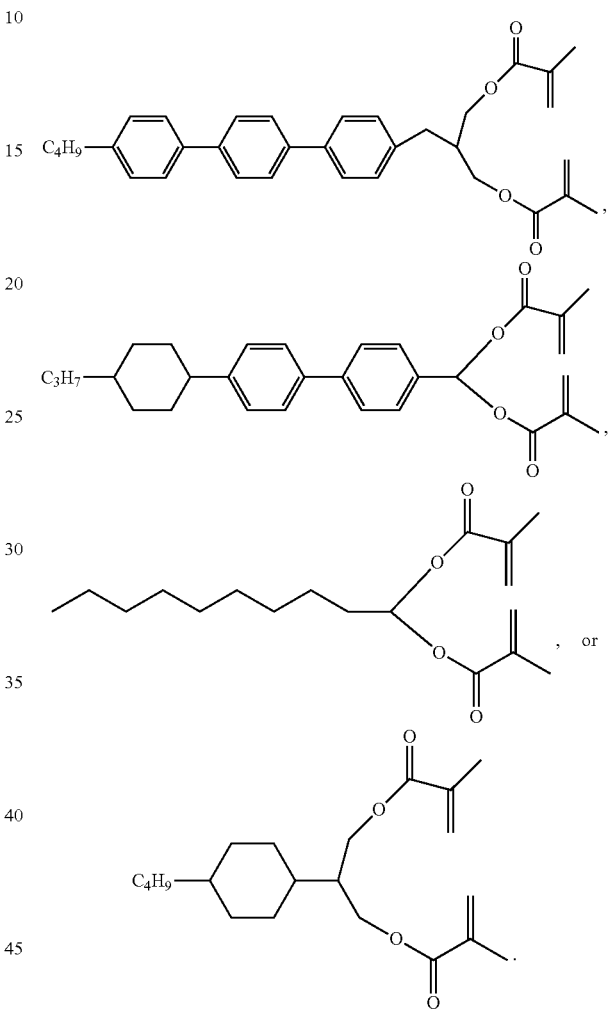

The benefits of the present invention are: the present invention provides thermal crosslink material, a manufacture method of a liquid crystal display panel and a liquid crystal display panel; a structural formula of the thermal crosslink material according to the present invention is

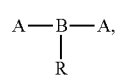

wherein A is

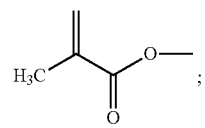

B is

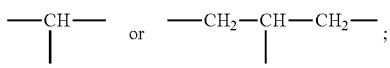

R is a linear or chain branched alkyl having 5-20 C atoms, and a first group obtained after some $CH_2$ group in the alkyl is replaced by phenyl, cycloalkyl, —O—, —CONH—, —COO—, —O—CO—, —CO—, or —CH=CH— group, or a second group obtained after the alkyl and some H atom in the first group are replaced by F atom or Cl atom; the thermal crosslink material belongs to an organic material of Methacrylic acid, and in a heating condition, the crosslinking reaction can be generated among the molecules to form macromolecular polymer having crosslinked network, and after mixing the thermal crosslink material in the liquid crystal material to be heated to form the polymer, the head groups A and B can be anchored on the substrate surface after the phase separation, and the branch R can act the result of vertical alignment, and thus to form the alignment films. Consequently, the manufacture cost of the TFT-LCD can be reduced and the capacity can be promoted; in the manufacture of the liquid crystal display panel according to the present invention, by adding the thermal crosslink material in the liquid crystal compound of the liquid crystal display panel to form the alignment films on the surfaces of opposite sides of the TFT substrate and the CF substrate to simplify the manufacture process and to reduce the production cost. Besides, the crosslinking reaction can be generated among the molecules of the thermal crosslink material in the heating condition. In comparison with the PSVA type display panel, the additional Reactive Monomer (RM) is not necessary, and one ultraviolet light irradiation process can be omitted; in the liquid crystal display panel of the present invention, the alignment films are polymer, which is formed by that the thermal crosslink material mixed in the liquid crystal material is generated with the crosslinking reaction in a heating condition, and is deposed on the surfaces of opposite sides of the TFT substrate and the color film substrate. Then, the PI alignment films can be eliminated, and the manufacture process of the TFT-LCD can be simplified to significantly reduce the manufacture cost of the TFT-LCD, and the alignment result of the liquid crystal is great.

BRIEF DESCRIPTION OF THE DRAWINGS

In order to better understand the characteristics and technical aspect of the invention, please refer to the following detailed description of the present invention is concerned with the diagrams, however, provide reference to the accompanying drawings and description only and is not intended to be limiting of the invention.

In drawings.

DETAILED DESCRIPTION OF PREFERRED EMBODIMENTS

For better explaining the technical solution and the effect of the present invention, the present invention will be further described in detail with the accompanying drawings and the specific embodiments.

The present invention first provides thermal crosslink material, employed to be alignment film material, and a structural formula thereof is

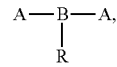

wherein

A is

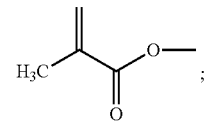

B is

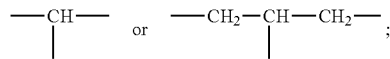

R is a linear or chain branched alkyl having 5-20 C atoms, and a first group obtained after some $CH_2$ group in the alkyl is replaced by phenyl, cycloalkyl, —O—, —CONH—, —COO—, —O—CO—, —CO—, or —CH=CH— group, or a second group obtained after the alkyl and some H atom in the first group are replaced by F atom or Cl atom.

Figure 1:
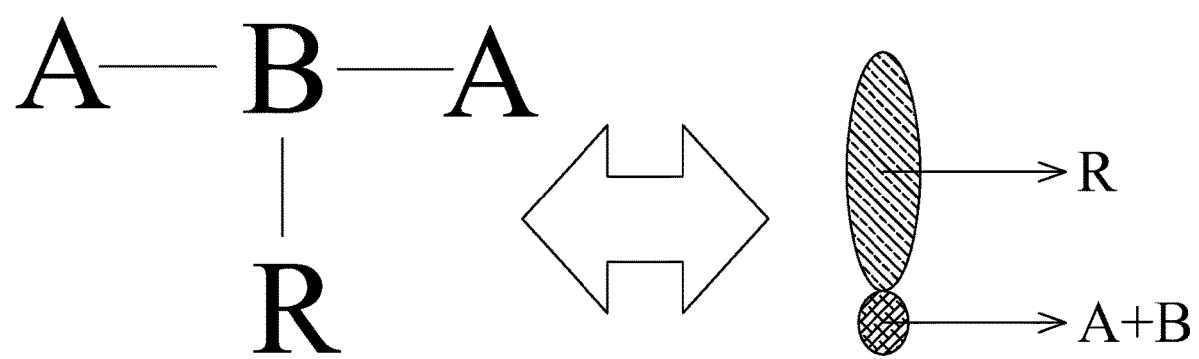
FIG. 1 is a structure diagram of thermal crosslink material according to the present invention.

Specifically, as shown in FIG. 1, in the thermal crosslink material, the A and the B belongs to the head group, and the head group comprises two or more double bond groups. The main function thereof is to generate thermal crosslink reaction at the certain temperature; the main function of the tail group R is similar to the function of the PI branch to vertically align the liquid crystal molecules in the steric hindrance manner.

Preferably, a structural formula of the thermal crosslink material is:

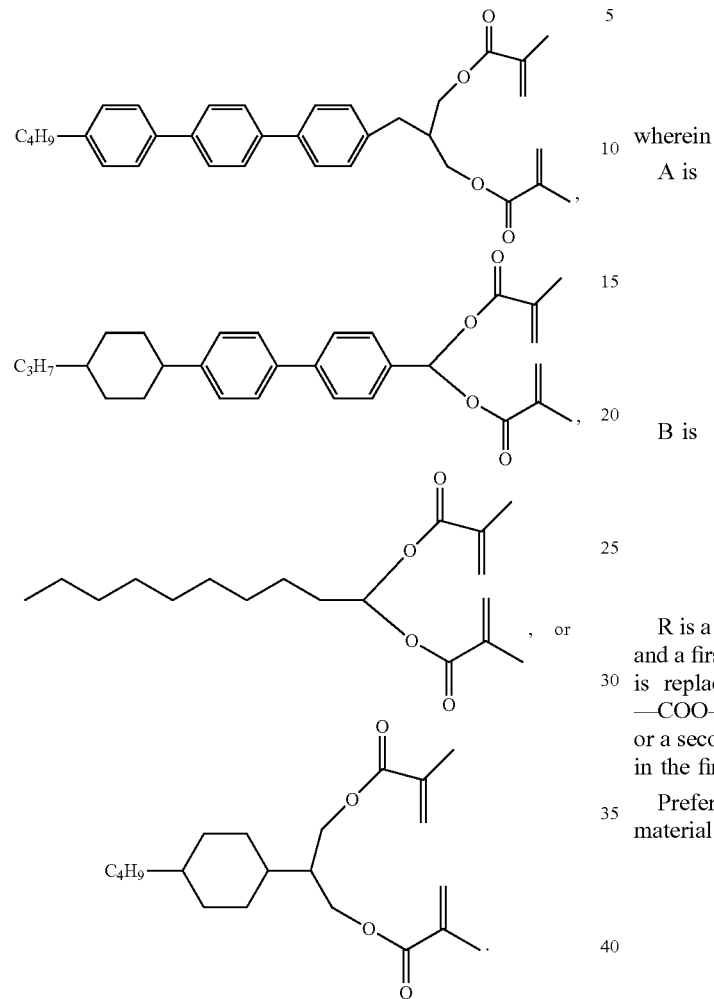

Figure 2:
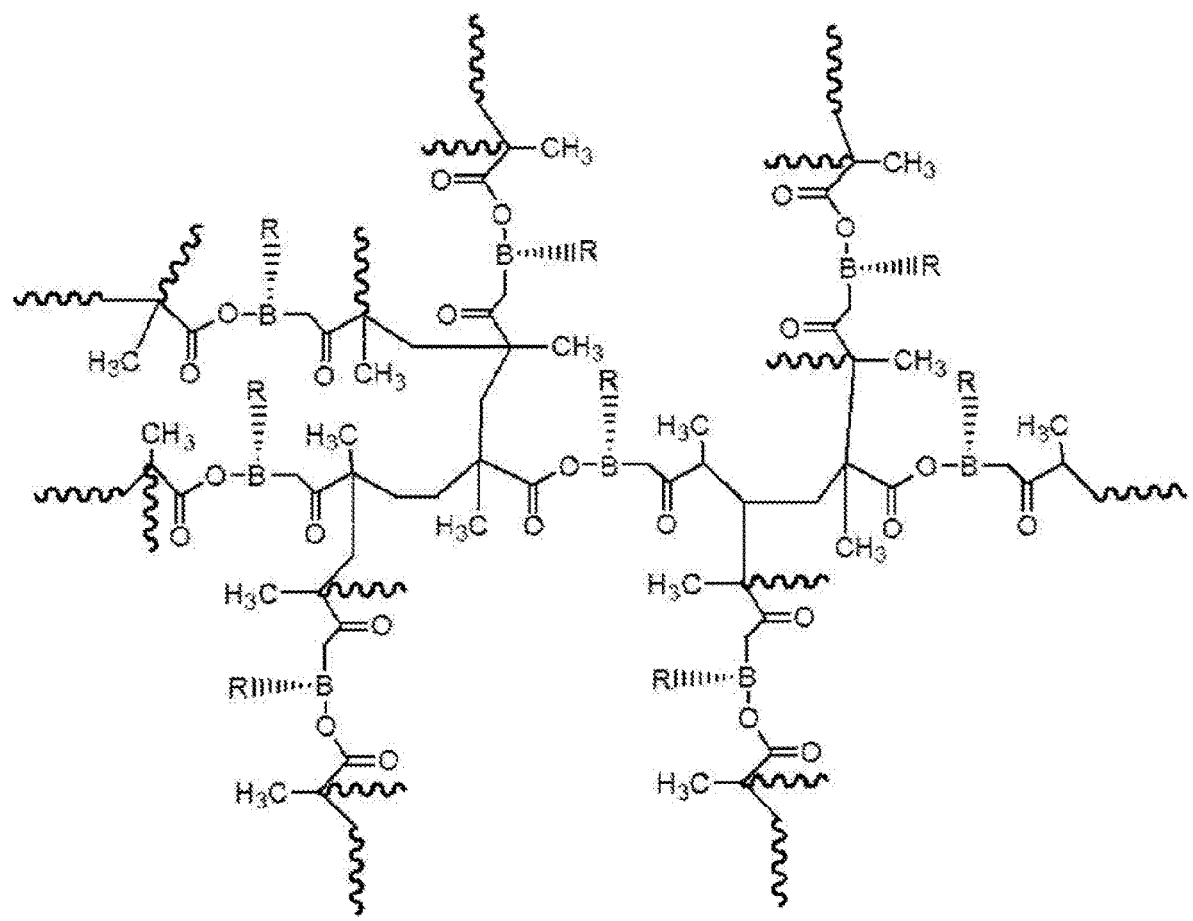
FIG. 2 is a structure diagram of polymer formed by that the thermal crosslink material of the present invention is heated and generated with the crosslinking reaction.

The thermal crosslink material provided by the present invention belongs to an organic material of Methacrylic acid. As shown in FIG. 2, in a heating condition, the crosslinking reaction can be generated among the molecules to form macromolecular polymer having crosslinked network. Then, after mixing the thermal crosslink material in the liquid crystal material to be heated to form the polymer, the head groups A and B can be anchored on the substrate surface after the phase separation, and the branch R can act the result of vertical alignment, and thus to form the alignment films. Consequently, the liquid crystal display panel utilizing the thermal crosslink material can eliminate the PI alignment films. The manufacture process of the TFT-LCD can be simplified to significantly reduce the manufacture cost of the TFT-LCD.

Figure 3:
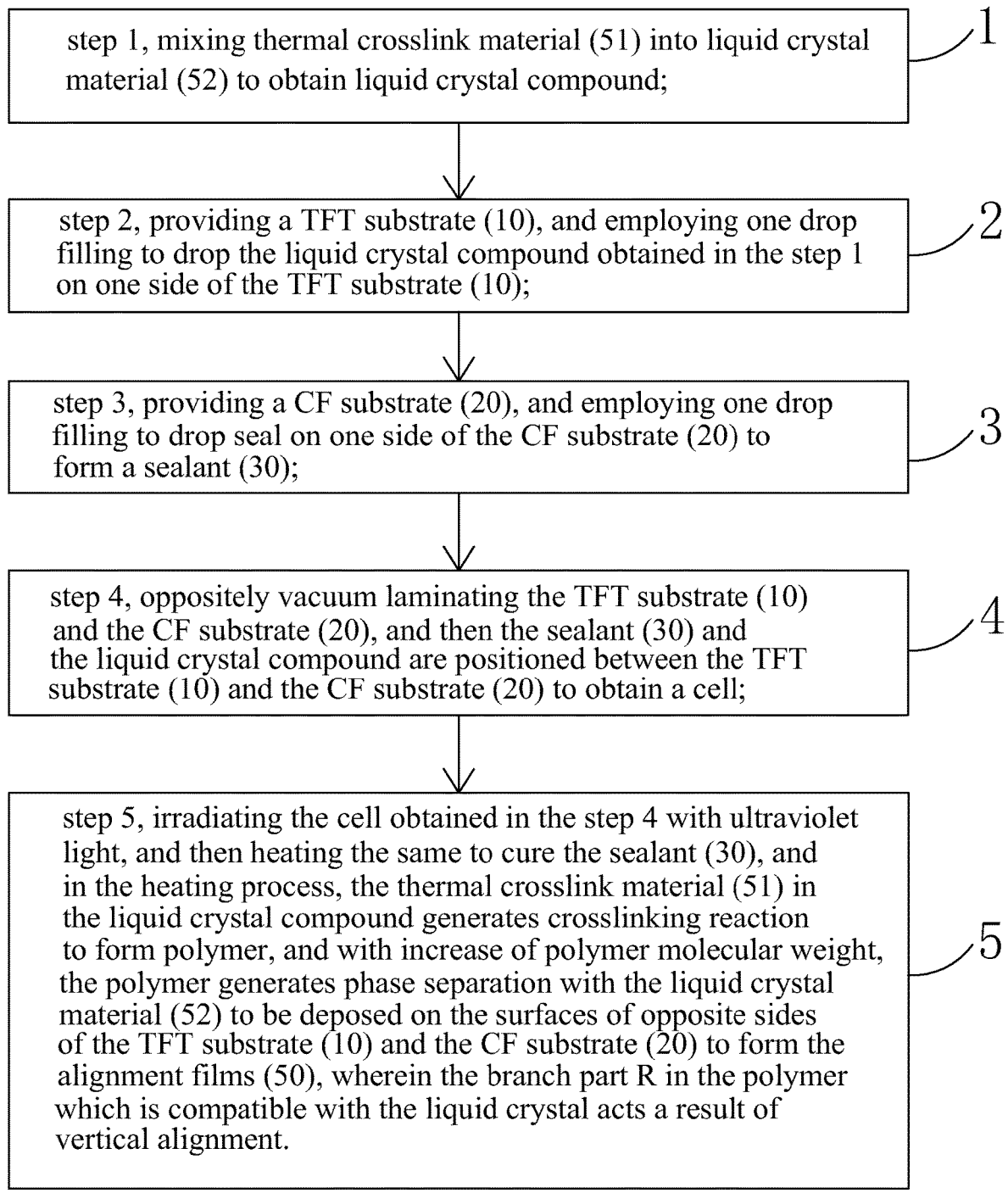
FIG. 3 is a flowchart of a manufacture method of a liquid crystal display panel according to the present invention.

Please refer to FIG. 3, the present invention further provides a manufacture method of a liquid crystal display panel, comprising steps of:

step 1, mixing thermal crosslink material 51 into liquid crystal material 52 to obtain liquid crystal compound;

a structural formula of the thermal crosslink material 51 is

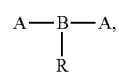

wherein
A is

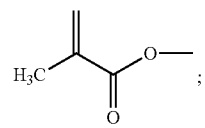

B is

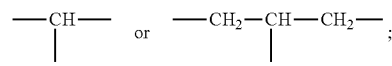

R is a linear or chain branched alkyl having 5-20 C atoms, and a first group obtained after some $CH_2$ group in the alkyl is replaced by phenyl, cycloalkyl, —O—, —CONH—, —COO—, —O—CO—, —CO—, or —CH=CH— group, or a second group obtained after the alkyl and some H atom in the first group are replaced by F atom or Cl atom;

Preferably, a structural formula of the thermal crosslink material 51 is:

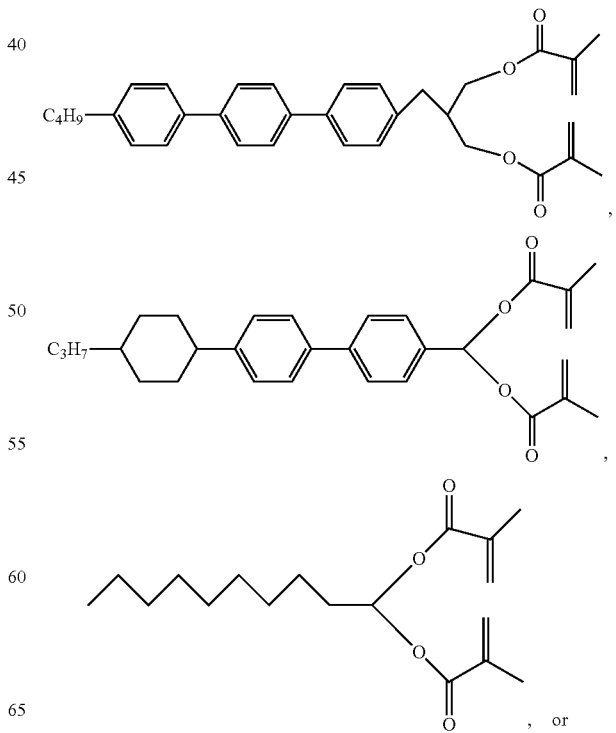

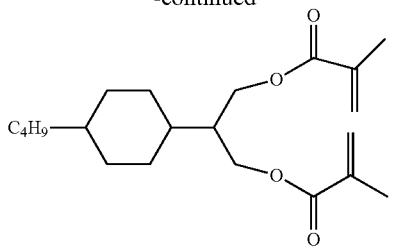

Figure 4:
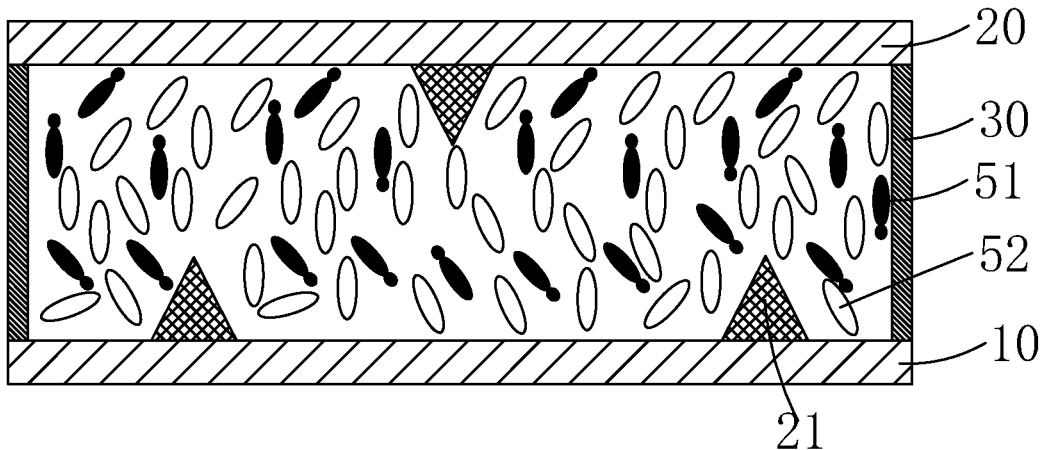
FIG. 4 is a diagram of step 4 in the manufacture method of the liquid crystal display panel according to the present invention.
Figure 5:
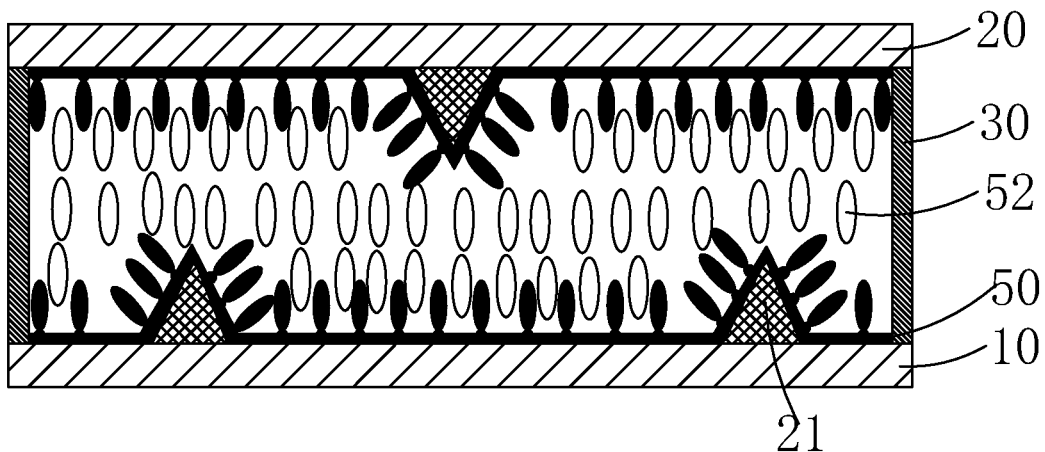
FIG. 5 is a diagram of step 5 in the manufacture method of the liquid crystal display panel according to the present invention, and a liquid crystal distribution diagram of the liquid crystal display panel of the present invention without being applied with power.

Specifically, in the liquid crystal compound obtained in the step 1, a content of the thermal crosslink material 51 is 0.1-5 wt %.

step 2, providing a TFT substrate 10, and employing one drop filling (ODF) to drop the liquid crystal compound obtained in the step 1 on one side of the TFT substrate 10;

step 3, providing a CF substrate 20, and employing one drop filling to drop seal on one side of the CF substrate 20 to form a sealant 30;

step 4, as shown in FIG. 4, oppositely vacuum laminating the TFT substrate 10 and the CF substrate 20, and then the sealant 30 and the liquid crystal compound are positioned between the TFT substrate 10 and the CF substrate 20 to obtain a cell;

then, the thermal crosslink material 51 is still mixed in the liquid crystal material 52, and the crosslinking reaction has not generated, and has not acted alignment function to the liquid crystal material 52.

step 5, as shown in FIG. 5, irradiating the cell obtained in the step 4 with ultraviolet light, and then heating the same to cure the sealant 30, and in the heating process, the thermal crosslink material 51 in the liquid crystal compound generates crosslinking reaction to form polymer, and with increase of polymer molecular weight, the polymer generates phase separation with the liquid crystal material 52 to be deposed on the surfaces of opposite sides of the TFT substrate 10 and the CF substrate 20 to form the alignment films 50, wherein the branch part R in the polymer which is compatible with the liquid crystal acts a result of vertical alignment.

Specifically, in the step 5, an irradiation intensity of the ultraviolet light is 50-100 mW/cm², and an irradiation period is 1-5 min, and a heating temperature is 110-130° C., and a heating period is 20-30 min.

Specifically, the liquid crystal display panel is a multi-domain vertical alignment (MVA) type liquid crystal display panel, and the TFT substrate provided in the step 2 is a TFT substrate of the traditional MVA type liquid crystal display panel, and a plurality of roof shape projections 21 are provided on the one side of the TFT substrate where the liquid crystal compound is pre-dropped, and the CF substrate provided in the step 3 is a CF substrate of the traditional MVA type liquid crystal display panel, and a plurality of roof shape projections 21 are provided on the one side of the CF substrate where the sealant is pre-dropped.

Figure 6:
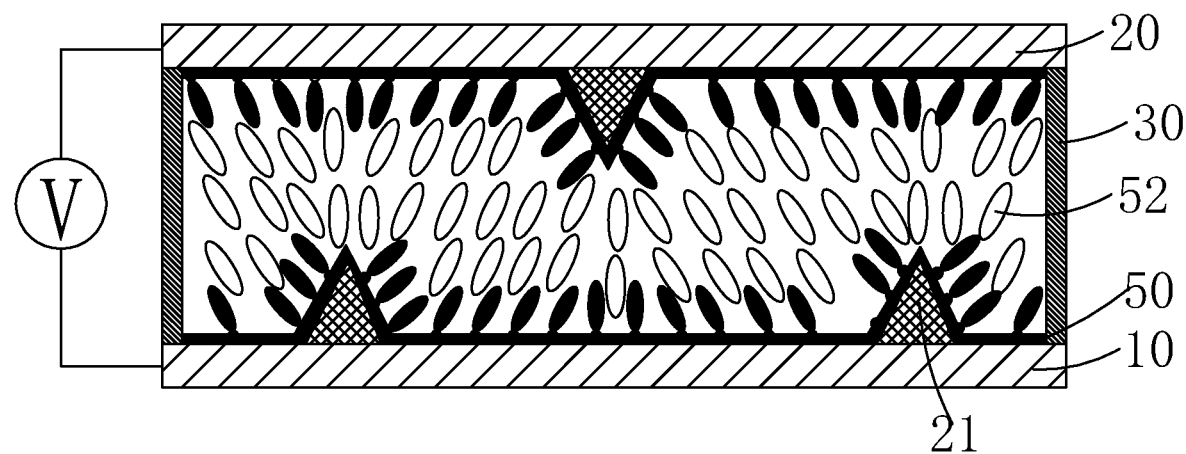
FIG. 6 is a liquid crystal distribution diagram of the liquid crystal display panel of the present invention with being applied with power.

Specifically, pixel electrodes are provided on the one side of the TFT substrate provided in the step 2 where the liquid crystal compound is pre-dropped, and a common electrode is provided on the one side of the CF substrate provided in the step 3 where the sealant is pre-dropped. As shown in FIG. 6, by applying voltages to the pixel electrodes on the TFT substrate and the common electrode on the CF substrate of the manufactured liquid crystal display panel, the liquid crystal material 52 are acted by the common function of the projections 21 and the alignment films 50 to be aligned according to the slope inclination of the projections 21.

In the manufacture of the liquid crystal display panel according to the present invention, by adding the thermal crosslink material in the liquid crystal compound of the liquid crystal display panel to form the alignment films on the surfaces of opposite sides of the TFT substrate and the CF substrate to simplify the manufacture process and to reduce the production cost. Besides, the crosslinking reaction can be generated among the molecules of the thermal crosslink material in the heating condition. In comparison with the PSVA type display panel, the additional Reactive Monomer (RM) is not necessary, and one ultraviolet light irradiation process can be omitted.

Please refer to FIGS. 5-6, the present invention further provides a liquid crystal display panel, comprising a TFT substrate 10 and a CF substrate 20 which are oppositely positioned, and a liquid crystal layer sandwiched between the TFT substrate 10 and the CF substrate 20, a sealant 30 employed for sealing the TFT substrate 10 and the CF substrate 20, and alignment films 50 formed at surfaces of the TFT substrate 10 and the CF substrate 20 facing the liquid crystal layer;

a plurality of roof shape projections 21 are provided on sides of the TFT substrate 10 and the CF substrate 20 facing the liquid crystal layer;

the liquid crystal layer comprises liquid crystal material 52;

the alignment films 50 are polymer, which is formed by that the thermal crosslink material 51 in the liquid crystal material 52 is generated with the crosslinking reaction in a heating condition, and is deposed on the surfaces of opposite sides of the TFT substrate 10 and the CF substrate 20;

a structural formula of the thermal crosslink material 51 is

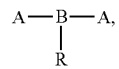

wherein

A is

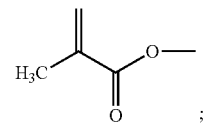

B is

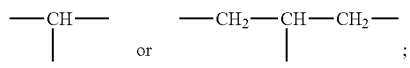

R is a linear or chain branched alkyl having 5-20 C atoms, and a first group obtained after some CH₂ group in the alkyl is replaced by phenyl, cycloalkyl, —O—, —CONH—, —COO—, —O—CO—, —CO—, or —CH=CH— group, or a second group obtained after the alkyl and some H atom in the first group are replaced by F atom or Cl atom.

Preferably, a structural formula of the thermal crosslink material 51 is:

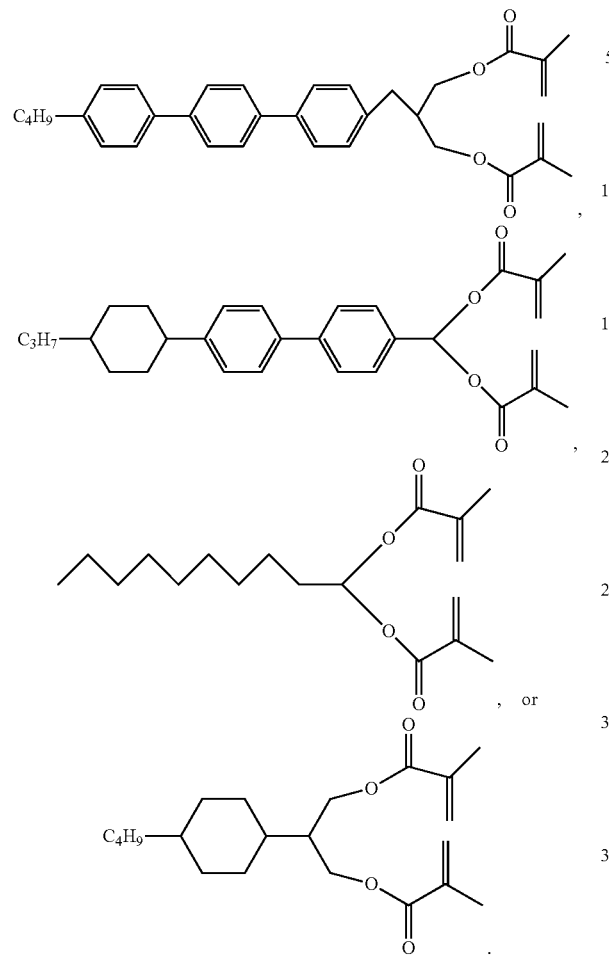
, or

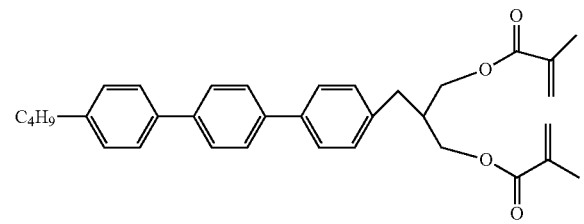
is:

Specifically, the pixel electrodes and the common electrode are respectively provided on opposite sides of the TFT substrate 10 and the CF substrate 20. As shown in FIG. 5, in condition that the voltage is not applied to the liquid crystal display panel, the liquid crystal material 52 is acted by the function of the alignment films 50 to be vertically aligned. As shown in FIG. 6, by applying voltages to the pixel electrodes 10 on the TFT substrate and the common electrode 20 on the CF substrate of the manufactured liquid crystal display panel, the liquid crystal material 52 are acted by the common function of the projections 21 and the alignment films 50 to be aligned according to the slope inclination of the projections 21.

Figure 7:
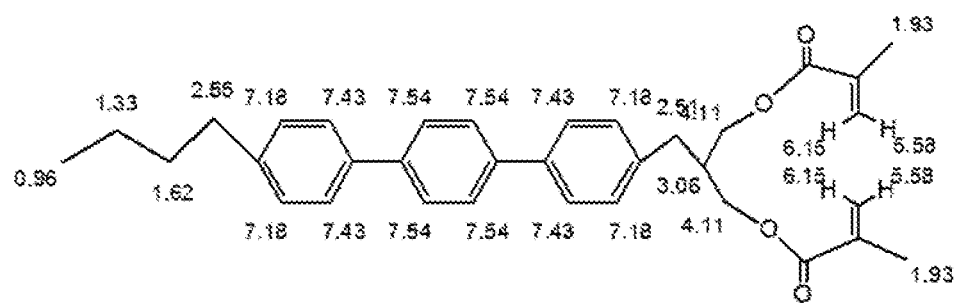
FIG. 7 is a nuclear magnetic resonance data analysis diagram of the manufactured thermal crosslink material of the specific structure.

A manufacture method of thermal crosslink material of the specific structure is shown in the following specific embodiment:

the manufacture method of the thermal crosslink material is:

weighting and measuring the glycol compound (I) and the acrylic acid (II) according to the mole ratio of glycol compound (I):the acrylic acid (II)=1:1.5-2, and putting the prepared glycol compound (I) and acrylic acid (II) in the reactor, and then using the sulfuric acid solution of mass fraction 85-90% to be the catalytic agent to react 4-6 hours at 100-130° C. to obtain the compound (III);

The reaction formula of the aforesaid reaction is below:

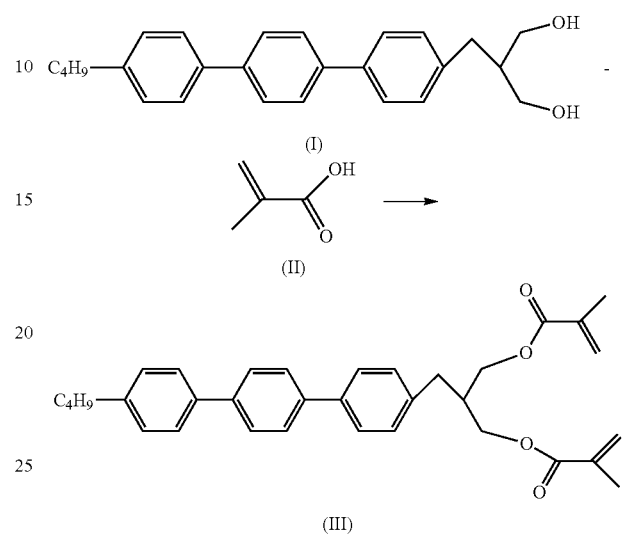

executing the nuclear magnetic resonance analysis to the obtained compound (III), and the obtained nuclear magnetic resonance data is: δ=0.96 (3H), δ=1.33 (2H), δ=1.62 (2H), δ=2.55 (2H), δ=7.18 (4H), δ=7.43 (4H), δ=7.54 (4H), δ=2.51 (2H), δ=3.06 (1H), δ=4.11 (4H), δ=1.93 (6H), δ=6.15 (2H), δ=5.58 (2H);

as shown in FIG. 7, thus, it can be ensured that the structural formula of the compound (III) is

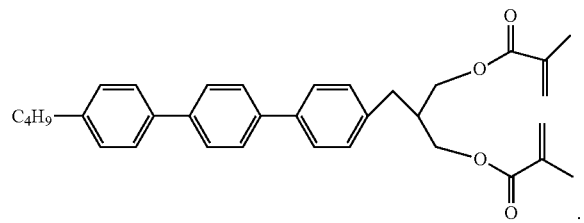

In conclusion, the present invention provides thermal crosslink material, a manufacture method of a liquid crystal display panel and a liquid crystal display panel; a structural formula of the thermal crosslink material according to the present invention is

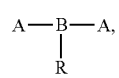

wherein A is

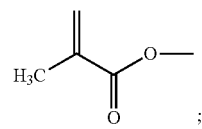

B is

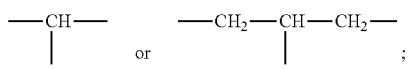

R is a linear or chain branched alkyl having 5-20 C atoms, and a first group obtained after some $CH_2$ group in the alkyl is replaced by phenyl, cycloalkyl, —O—, —CONH—, —COO—, —O—CO—, —CO—, or —CH=CH— group, or a second group obtained after the alkyl and some H atom in the first group are replaced by F atom or Cl atom; the thermal crosslink material belongs to an organic material of Methacrylic acid, and in a heating condition, the crosslinking reaction can be generated among the molecules to form macromolecular polymer having crosslinked network, and after mixing the thermal crosslink material in the liquid crystal material to be heated to form the polymer, the head groups A and B can be anchored on the substrate surface after the phase separation, and the branch R can act the result of vertical alignment, and thus to form the alignment films. Consequently, the manufacture cost of the TFT-LCD can be reduced and the capacity can be promoted; in the manufacture of the liquid crystal display panel according to the present invention, by adding the thermal crosslink material in the liquid crystal compound of the liquid crystal display panel to form the alignment films on the surfaces of opposite sides of the TFT substrate and the CF substrate to simplify the manufacture process and to reduce the production cost. Besides, the crosslinking reaction can be generated among the molecules of the thermal crosslink material in the heating condition. In comparison with the PSVA type display panel, the additional Reactive Monomer (RM) is not necessary, and one ultraviolet light irradiation process can be omitted; in the liquid crystal display panel of the present invention, the alignment films are polymer, which is formed by that the thermal crosslink material mixed in the liquid crystal material is generated with the crosslinking reaction in a heating condition, and is deposed on the surfaces of opposite sides of the TFT substrate and the color film substrate. Then, the PI alignment films can be eliminated, and the manufacture process of the TFT-LCD can be simplified to significantly reduce the manufacture cost of the TFT-LCD, and the alignment result of the liquid crystal is great.

Above are only specific embodiments of the present invention, the scope of the present invention is not limited to this, and to any persons who are skilled in the art, change or replacement which is easily derived should be covered by the protected scope of the invention. Thus, the protected scope of the invention should go by the subject claims.

What is claimed is:

1. A thermal crosslink material, which is employed as an alignment film material, the thermal crosslink material being represented by $$A-B-A, \atop R$$

where

A is

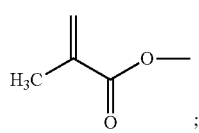

B is

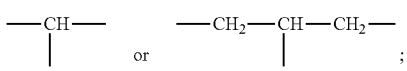

and

R is a linear or chain branched alkyl having 5 to 20 carbon atoms, wherein one or more $CH_2$ group in the alkyl is substituted with phenyl, cycloalkyl, —O—, —CONH—, —COO—, —O—CO—, —CO—, or —CH=CH— group, or one or more hydrogen atoms in the alkyl or substituted alkyl are substituted with F atom or Cl atom; and wherein a structural formula of the thermal crosslink material is:

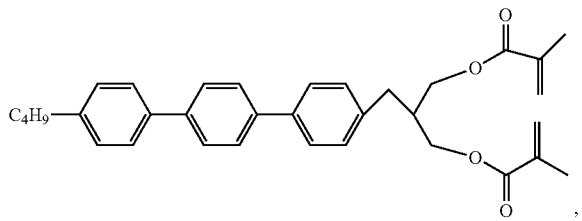

,

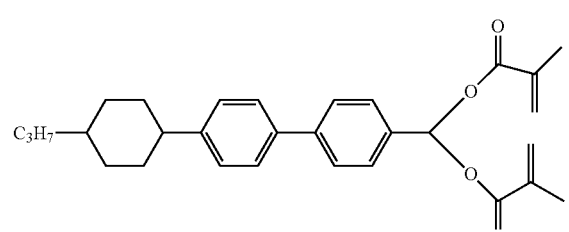

,

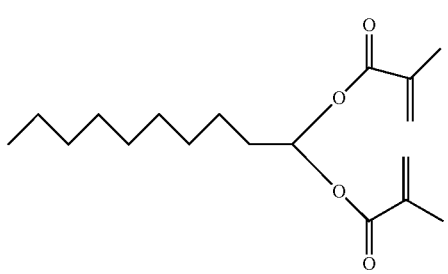

, or

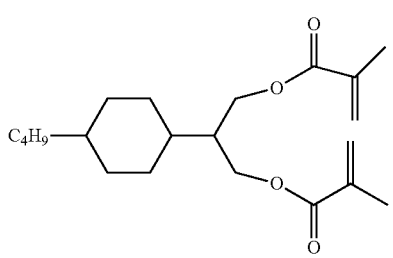

.

* * * * *